United States Patent [19]

Robins et al.

[11] 4,038,480

[45] July 26, 1977

[54] 6-AMINOCARBONYL PURINE 3',5'-CYCLIC NUCLEOTIDES

[75] Inventors: Roland K. Robins, Santa Ana; Dennis A. Shuman; Kay H. Boswell, both of Mission Viejo, all of Calif.

[73] Assignee: ICN Pharmaceuticals Inc., Irvine, Calif.

[21] Appl. No.: 398,009

[22] Filed: Sept. 17, 1973

[51] Int. Cl.$^2$ ............................................. C07H 19/20
[52] U.S. Cl. ...................................... 536/27; 424/180; 536/28
[58] Field of Search ................... 260/211.5 R; 536/27, 536/28

[56] References Cited

U.S. PATENT DOCUMENTS

| 3,380,996 | 4/1968 | Hondo et al. | 260/211.5 R |
| 3,535,207 | 10/1970 | Shiro et al. | 260/211.5 R |
| 3,712,885 | 1/1973 | Weimann et al. | 260/211.5 R |

Primary Examiner—Johnnie R. Brown
Attorney, Agent, or Firm—Kay H. Boswell; Thomas D. Kiley

[57] ABSTRACT

N$^6$-Carbamoyl and -carbonyl analogs of adenosine 3',5'-cyclic phosphate (cAMP) are prepared and variously demonstrated to exhibit kinase, adrenal steroidogenisis and lipolysis activation superior to cAMP, inhibit phosphodiesterase, and found to increase cardiac output or, in particular cases, to lower blood pressure.

22 Claims, 1 Drawing Figure

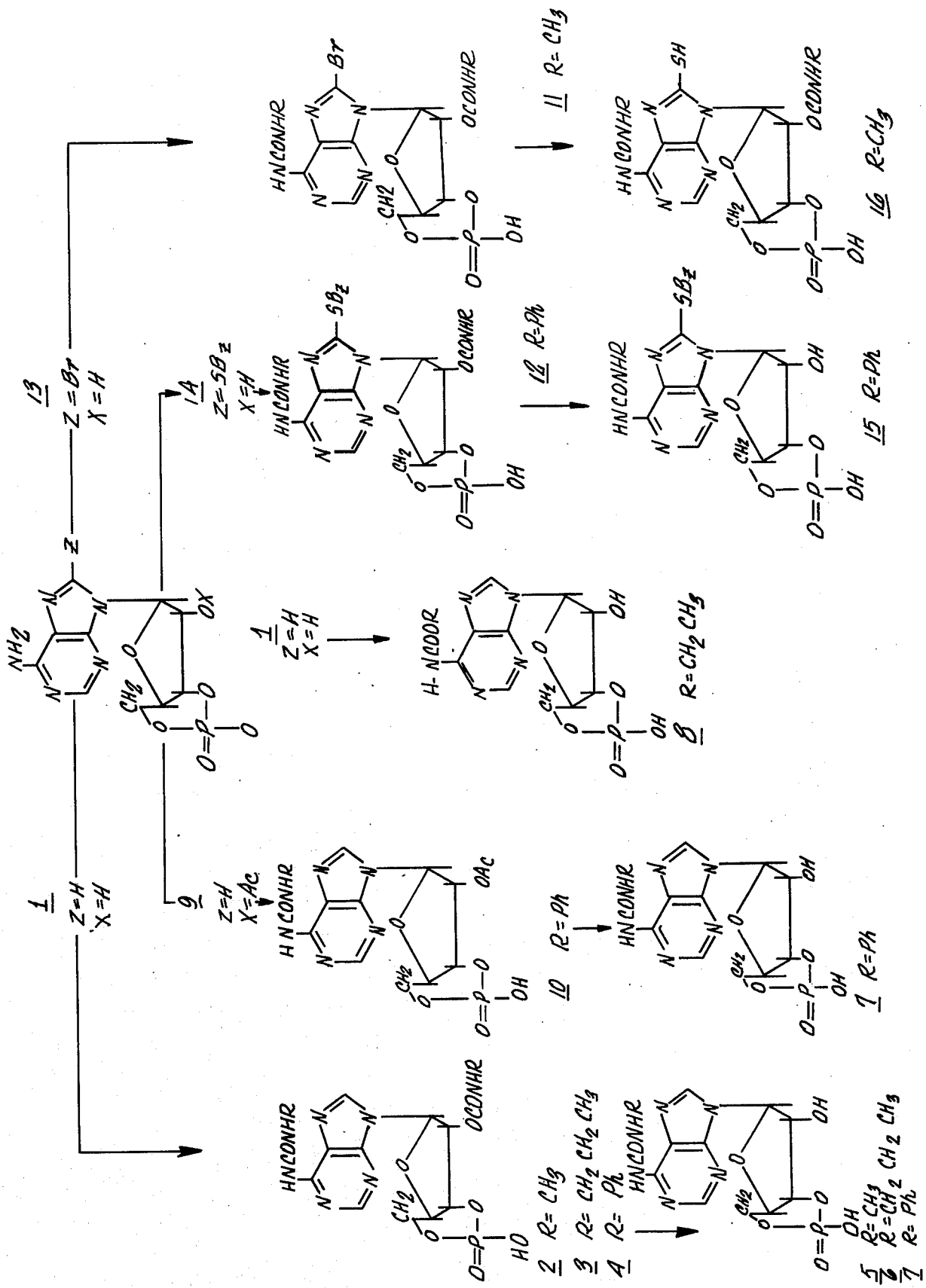

6-AMINOCARBONYL PURINE 3',5'-CYCLIC NUCLEOTIDES

BACKGROUND AND BRIEF SUMMARY OF THE INVENTION

Numerous $N^6$- carbamoyl and -carbonyl purines have been prepared, eg, Giner-Sorolla et al, *J. Am. Chem. Soc.* 80, 3932 (1958) and A. S. Jones et al, *Tetranhedron Letters* 26, 791 (1970). The ureidopurines N-(purin-6-ylcarbamoyl) threonine, N-(purin-6-ylmethylcarbamoyl) threonine and N(purin-6-ylcarbamoyl) glycine have been found to occur naturally as their riboside in tRNA. See G. B. Chedda et al, *Biochem.* 8, 3278 (1969), M. P. Schweizer et al, ibid.,8, 3283 (1969). M. P. Schweizer et al, ibid., 40, 1046 (1970) and H. Ishikura, *Biochem. Biophys. Res. Commun.* 37, 90 (1969). N-(purin-6-ylcarbamoyl) threonine has also been identified in human urine. G. B. Chedda, *Life Sci.* 8, 979 (1969). Several ureidopurine derivatives related to N-(purin-6-ylcarbamoyl) threonine have been synthesized and found to have cytokinin like growth-promoting properties. See C. I. Hong et al, *J. Med. Chem.* 16, 139 (1973) and R. H. Hall et al, *Cancer Res.* 31, 704 (1971). C. I. Hong et al, *Abstracts*, 162d Am. Chem. Soc. Nat'l. Meeting, Wash. D.C. (Sept 1971) have prepared 5'-phosphates of a number of naturally occuring 6-ureidopurine nucleosides, including those of structure

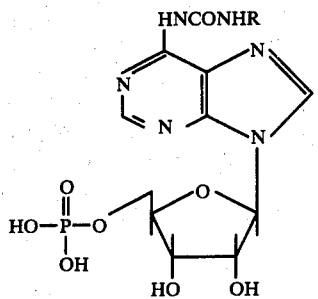

wherein R was alkyl or aryl. Adenosine 3', 5'-cyclic phosphate (cAMP, 1) has been well established as a mediator of many hormonal effects, and numerous of its 8-substituted derivatives have been prepared and demonstrated to possess physiological activity. Eg, U.S. Pat. No. 3,712,885 to Weimann et al.

According to this invention, there are prepared novel cyclic nucleotides of structure

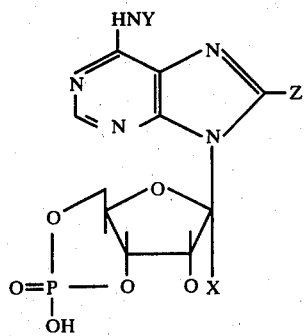

wherein Y is $COOR_1$, $CONHR_1$ or $CONHC_6H_5$, X is acyl, H or Y, Z is H, halogen or $SR_2$, $R_1$ is $C_1$ - $C_6$ alkyl and $R_2$ is H, phenyl, benzyl or $C_1$ - $C_6$ alkyl. The manner in which these compounds with the advantage of their properties previously referred to are obtained will appear from the detailed description which follows.

DETAILED DESCRIPTION OF THE INVENTION

N-alkyl and N-phenyl-$N^6$, 2'-O-bis-carbamoyladenosine 3',5'-cyclic phosphates (eg, 2, 3 and 4) are prepared by treatment of cAMP (1) with corresponding alkyl or phenyl isocyanates at, eg, 60°-80° C. Selective deblocking with refluxing $NaOCH_3$ or aqueous NaOH at room temperature affords the corresponding $N^6$-carbamoyl adenosine 3',5'-cyclic phosphates (eg, 5, 6 and 7). The latter compounds may alternatively be secured, without intermediate formation of the $N^6$,2'-O-bis-carbamoyladenosine nucleotide, by acyl blocking of the 2'-O position of 1 prior to reaction with isocyanate, followed by deblocking during workup. Thus, for example, phenylisocyanate and 2'-O-acetyladenosine 3',5'-cyclic phosphate (9) afford the correspondingly 2'-O-acyl blocked N-phenyl-$N^6$-carbamoyladenosine cyclic nucleotide 10 and, following workup, the deblocked nucleotide 7.

Treatment of 1 with an appropriately chosen alkylchloroformate (eg, ethylchloroformate for $N^6$-ethoxycarbonyl-cAMP, 8) followed by treatment with 2 N NaOH affords the $N^6$-alkoxycarbonyl-cAMP derivatives.

8-Benzylthio-$N^6$,2'-O-bis-(N-pheylcarbamoyl)-cAMP (12) is afforded by direct treatment of 8-benzylthio-cAMP [K. Muneyama et al, *Biochem.* 10, 2390 (1971)] with phenylisocyanate, and basic hydrolysis affords 8-benzylthio-$N^6$-(N-phenylcarbamoyl)-cAMP (15). The corresponding 8-phenyl compounds are analogously obtained. Corresponding $N^6$-(N-alkylcarbamoyl) compounds are obtained simply by appropriate choice of isocyanate reactant.

8-Halogenated cAMP compounds (eg, 8-bromo-cAMP, K. Muneyama et al, *Biochem.* 10, 2390 (1971) and 8-chloro-cAMP, Robins et al, U.S. Pat. application Ser. No. 153,413 (filed June 15, 1971 and now abandoned) whose disclosure is incorporated herein by reference) afford access, through initial formation of 8-halo-$N^6$-mono- and $N^6$,2'-O-bis-(N-alkyl-, N-phenyl-, carbamoyl)-cAMP derivatives, to otherwise 8-substituted $N^6$-mono- and $N^6$,2'-O-bis-(n-alkyl-, N-phenyl-, carbamoyl)-cAMP derivatives by nucleophilic substitution of the 8-halo moiety. For example, treatment of 8-bromo-$N^6$,2'-O-bis-(N-methyl carbamoyl)-cAMP (11) with thiourea affords 8-thio-$N^6$,2'-O-bis-(N-methyl carbamoyl)-cAMP (16). The 8-thio group can be alkylated with, eg, $C_1$-$C_6$ alkyl halides to form 8-alkylthio $N^6$-mono- and $N^6$,2'-O-bis-(N-alkyl- or or N-phenyl-, carbamoyl)-cAMP compounds and, employing α-bromotoluene, alkylation affords an alternative route to 8-benzylthio analogs such as 12 and 15.

2'-O-acylated N-alkyl- and N-phenyl-carbamoyl cyclic nucleotides are useful intermediates (eg, compound 10) and bioactive end products can be similarly acylated to enhance lipid solubility, etc. The O-acylated (eg, $C_1$-$C_{18}$ acyl) analogs may be secured by reacting the free nucleotides with corresponding acid anhydrides or acyl halides (eg, acetyl, butyryl, hexanoyl, lauryl, adamantoyl, etc.). Sutherland et al, in *Biochim. et Biophys. Acta* 148, 106 (1967) have demonstrated that acylation enhances cellular transport of purine nucleotides. Especially preferred are the 2'-O-butyryl derivatives prepared by reacting free nucleoside and butyric anhydride at room temperature in dimethyl formamide: 4-dimethylaminopyridine.

In the Examples of preferred embodiments which follow, evaporations were performed under diminished pressure at less than 40° C. The structures of carbamoyl and carbonyl derivatives of cAMP were verified by pmr, uv spectra and elemental analysis, the latter analysis results lying within ±0.3% of theoretical values where reported by reference to elemental designation (e.g., "C,H,N"). UV spectra were determined on a Cary 15 spectrometer. Silica gel for column chromatograhy was E. M. Reagent Silica Gel 60 (particle size 0.063–0.200 nm). The eluates from column chromatography were monitored at 254 nm to detect the presence of uv absorbing compounds. All samples were dried over $CaSO_4$ at 100° under high vacuum. All temperatures are in ° C.

EXAMPLE 1

$N^6$, 2'-O-bis-(N-Methylcarbamoyl)adenosine 3',5'-cyclic phosphate sodium salt (2).

A solution of 1.0 g (3.2 mmole) of cAMP (1), 1 ml $Et_3N$ and 3 ml methylisocyanate in 50 ml of DMF was heated at 80° overnight in a bomb. The solution was poured into 200 ml of $Et_2O$ and the $Et_2O$ decanted from the oil. The oil was again titurated with $Et_2O$ and decanted. The residue was dissolved in $CHCl_3$ and placed onto a 30 g column (2.5 cm D.) of silica gel (packed in $CHCl_3$). The column was washed with $CHCl_3$ and then eluted with $MeOH:CHCl_3$ (15:85) The appropriate fractions were pooled and taken to dryness in vacuo. The residue was dissolved in $H_2O$ and passed through a 50 ml column of Dowex 50 (Na+) resin. The column was eluted with $H_2O$ and the eluate was taken to dryness in vacuo and the residue dissolved in MeOH. Two volumes of EtOH were added at boil and the volume reduced until solid started separating out. the suspension was cooled and the solid filtered and dried to yield 412 mg (28%) of 2; $\lambda_{max}^{pH\ 1}$ nm ($\epsilon$ 23,100), $\lambda_{max}^{pH\ 7}$ 267 nm, 280 sh ($\epsilon$ 22,500, 21,500), $\lambda_{max}^{pH\ 11}$ 267 nm, 280 sh ($\epsilon$ 21,900, 18,600). Anal. ($C_{14}H_{17}N_7O_8NaP$) C, H, N, Na.

EXAMPLE 2

$N^6$, 2'-O-bis-(N-Propylcarbamoyl)adenosine 3',5'-cyclic phosphate sodium salt (3).

A solution of 7 g (21.3 mmole) of cAMP, 5 ml $Et_3N$ and 14 ml propylisocyanate in 80 ml of DMF was heated in a bomb at 70° overnight. The solvent was removed in vacuo and the residue co-distilled with $H_2O$ and then EtOH. The final residue was taken up in $CHCl_3$ and placed onto a column (2.5 cm D.) of 70 g of silica gel (packed in $CHCl_3$). The column was eluted with $CHCl_3$ to remove the urea and then with $MeOH:CHCl_3$ (1:9). The fractions containing product were pooled and reduced to dryness in vacuo. The residue was dissolved in a small volume of $H_2O$ and passed through a 4 × 15 cm column of Dowex 50 (Na+) resin. The column was eluted with $H_2O$ and the eluate reduced to dryness in vacuo. The residue was co-distilled with MeOH to dryness. The final residue was dissolved in a small volume of MeOH and 5 volumes of EtOAc added. The solid was filtered, washed with EtOAc, washed with $Et_2O$, and dried to yield 5.8 g (52%) of 3; $\lambda_{max}^{pH1}$ 276 nm ($\epsilon$ 24,900), ($\epsilon$ 24,900), $\lambda_{max}^{pH7}$ 267 nm, 275 sh ($\epsilon$ 23,500, 20,100), $\lambda_{max}^{pH11}$ 267 nm, 275 sh ($\epsilon$ 23,500, 20,100). Anal. ($C_{18}H_{25}N_7O_8NaP\cdot H_2O$) C, H, N, Na.

EXAMPLE 3

$N^6$, 2'-O-bis-(N-Phenylcarbamoyl)adenosine 3',5'-cyclic phosphate sodium salt (4).

A solution of 12.0 g 36.5 mmole) of cAMP (1), 10 ml $Et_3N$ and 25 ml phenylisocyanate in 400 ml DMF was stirred overnight in a 70° oil bath. The resulting solution was concentrated to ½ in vacuo and then partitioned between 200 ml of $H_2O$ and 200 ml of EtOAc. The aqueous phase was heated on a steam bath and the hot solution extracted four times with EtOAc. The final aqueous phase was warmed on a steam bath, 50 ml of a saturated NaCl solution was added, and the solution was cooled. The resulting crystals were filtered, washed with a small amount of cold $H_2O$ and recrystalized from an $H_2O:EtOH$ (1:4) mixture. The final solid was filtered, washed with EtOH and dried to yield 10 g (47%) of 4; $\lambda_{max}^{pH\ 1}$ 284 nm ($\epsilon$ 20,300), $\lambda_{max}^{pH\ 7}$ 231 nm, 276 ($\epsilon$ 18,200, 22,100). $\lambda_{max}^{pH\ 11}$ 233 nm, 276 ($\epsilon$ 17,200, 21,500), $\lambda_{max}^{pH\ 13}$ 307 nm ($\epsilon$ 29,100). Anal. ($C_{24}H_{21}N_7O_8NaP$) C, H, N, Na.

EXAMPLE 4

$N^6$-(N-Methylcarbamoyl) adenosine 3',5'-cyclic phosphate (5).

A solution of 5.0 g (15.2 mmole) of cAMP (1), 5 ml of $Et_3N$ and 10 ml of methylisocyanate in 50 ml of DMF was heated at 60° overnight in a bomb. The solvent was removed in vacuo and the residue co-distilled once with MeOH and then dissolved in 200 ml of MeOH containing 5 g of NaOMe. After refluxing for 8 hr, the solvent was removed in vacuo and the residue dissolved in $H_2O$. This solution was placed onto a column (4 cm D.) of 54 ml of Dowex 1 × 2(formate, 100–200 mesh). The column was washed with $H_2O$ and then eluted with a gradient of 800 ml of $H_2O$ in the mixing chamber and 800 ml of 6 N formic acid in the reservoir. Fractions of 25 ml were collected. Fractions 36 to 60 were pooled, reduced to dryness and the residue co-distilled with EtOH. The final residue was recrystallized from EtOH to yield, after drying, 2.66 g (50%) of 5; $\lambda_{max}^{pH\ 1}$ 276 nm ($\epsilon$ 22,900), $\lambda_{max}^{pH\ 7}$ 267 nm, 275 sh ($\epsilon$ 22,300, 19,000), $\lambda_{max}^{pH\ 11}$ 267 nm, 275 sh ($\epsilon$ 21,800, 18,500). Anal. ($C_{12}H_{15}N_6O_7P\cdot 3/4H_2O$) C, H, N.

EXAMPLE 5

$N^6$-(N-Propylcarbamoyl) adenosine 3',5'-cyclic phosphate (6).

A solution of 2.6 g (5.0 mmole) of $N^6$, 2'-O-(N-propylcarbamoyl) adenosine 3',5'-cyclic phosphate (3) and 3 g of NaOMe in 200 ml of absolute MeOH was refluxed for 9 hr. The solvent was removed and the residue dissolved in a small volume of $H_2O$ and placed onto a 25 ml column (2 cm D.) of Dowex 1 × 2 (formate, 100–200 mesh). The column was washed with $H_2O$ and then eluted with a gradient of 350 ml of $H_2O$ in the mixing chamber and 350 ml of 6 N formic acid in the reservoir. Elution was continued with 300 ml of 6 N formic acid. Fractions of 25 ml were collected after start of gradient. Fractions 27 through 39 were pooled and taken to dryness in vacuo. The residue was co-distilled with MeOH twice, slurried in EtOH, filtered and dried to yield 1.06 g (51%) of 6; $\lambda_{max}^{pH\ 1}$ 277 nm ($\epsilon$ 23,800), $\lambda_{max}^{pH\ 7}$ 268 nm, 276 sh ($\epsilon$ 22,700, 19,200), $\lambda_{max}^{pH\ 11}$ 268 nm, 276 sh ($\epsilon$ 22,200, 18,900), $\lambda_{max}^{pH\ 11}$ 268 nm, 276 sh ($\epsilon$ 22,200, 18,900), $\lambda_{max}^{pH\ 12.65}$ 277 nm, 296, 269 sh ($\epsilon$ 14,900, 16,600, 13,800). Anal. $C_{14}H_{19}N_6O_7P$) C, H, N.

EXAMPLE 6A $N^6$-(N-Phenylcarbamoyl)adenosine 3′,5′-cyclic phosphate (7).

Method A: A solution of 1.0 g (2.7 mmole) of 2′-O-acetyladenosine 3′,5′cyclic phosphate (9), 4 ml $Et_3N$ and 3 ml of phenylisocyanate in 50 ml of DMF was stirred overnight at room temperature. The solution was poured into 100 ml of $H_2O$ and stirred for ½ hr. The aqueous solution was extracted three times with 50 ml of $Et_2O$ and was reduced to dryness in vacuo. The residue was dissolved in 20 ml of 1 N NaOH and set aside for ½ hr. The pH was then adjusted to 1 with 1 N HCl. The crystals which formed were filtered, washed with $H_2O$ and dried to yield .33 87 g (26%) of 7:$\lambda_{max}^{pH\ 1}$ 285 nm ($\epsilon$ 28,300), $\lambda_{max}^{pH}$ 277 nm ($\epsilon$ 29,000), $\lambda_{max}^{pH\ 11}$ 277 nm ($\epsilon$ 28,600). Anal. ($C_{17}H_{17}N_6O_7P.1.5H_2O$) C, H, N.

EXAMPLE 6B $N^6$-(N-Phenylcarbamoyl) adenosine 3′,5′cyclic phosphate (7).

Method B: A solution of 9.0 g (15.3 mmole) of $N^6$, 2′-O-bis(N-phenylcarbamoyl)adenosine 3′,5′cyclic phosphate (4) in 75 ml of DMF and 45 ml of 2 N NaOH was stirred at room temperature for 2.5 hr. The solvent was removed in vacuo and the residue was partitioned between 100 ml of $H_2O$ and 100 ml of $Et_2O$. The aqueous phase was extracted three times with $Et_2O$ and then was acidified to pH 1 with 1 N HCl. The resulting solid was filtered, washed with $H_2O$ and dried to yield 6.2 g (85%) of 7.

EXAMPLE 7

$N^6$-(Ethoxycarbonyl)adenosine 3′5′-cyclic phosphate (8).

A hot solution of 6.0 g (18 mmole) of cAMP (1) and 5.2 of g of 4-morpholine-N-N′-dicyclohexylcarboxamidine in aqueous pyridine was co-distilled with pyridine to dryness. The residue was dissolved in 200 ml of pyridine, cooled at 0° and 15 ml of ethylchloroformate was added dropwise. The reaction mixture was allowed to warm to room temperature overnight and then 50 g of ice was added. After 4 hr the solvent was removed in vacuo and the residue co-distilled with EtOH:toluene to remove traces of pyridine. The residue was taken up in $H_2O$ and the pH adjusted to 11 with 2 N NaOH. After ½ hr the solution was neutralized with AcOH, placed onto a 500 ml column (4 cm D.) of Dowex 50 $\times$ 8 ($H^+$100–200 mesh) resin and eluted with $H_2O$. The first fractions yielded an impurity, followed by product and finally cAMP. The fractions containing the product were pooled, reduced in volume in vacuo and passed through a 100 ml column of Dowex 50 ($Na^+$) resin. The column was eluted with $H_2O$ and the eluate was reduced in vacuo to dryness. The residue was dissolved in boiling MeOH and two volumes of EtOH added slowly at boil. The volume was reduced at boil until solid appeared. After cooling, the solid was filtered and dried to yield 2.15 g (28%) of 8; $\lambda_{max}^{pH\ 1}$ 275 nm ($\epsilon$ 20,500), $\lambda_{max}^{pH\ 7}$ 267 nm ($\epsilon$ 19,000), $\lambda_{max}^{pH\ 11}$ 268 nm, 289, 275 sh ($\epsilon$ 14,500, 9,500, 13,900). Anal. ($C_{13}H_{15}N_5O_8NaP$) C, H, N, Na.

EXAMPLE 8

8-Bromo-$N^6$,2′-O-bis-(N-methylcarbamoyl)adenosine 3′,5′-cyclic phosphate

A solution of 1 g (2.4 mmole) of 8-bromoadenosine 3′,5′-cyclic phosphate (13)[12], 1, ml of $Et_3N$ and 2 ml methylisocyanate in 40 ml of DMF was heated at 70° overnight. After cooling to room temperature, the solution was partitioned between 150 ml of $H_2O$ and 150 ml of EtOAc. The aqueous phase was extracted three times with 150 ml of EtOAc and then placed onto a 17 ml column (2 cm D.) of Dowex 1 $\times$ 2 (formate, 100–200 mesh. The column was eluted with a gradient of 600 ml of $H_2O$ in the mixing chamber and 600 ml of 6 N formic acid in the reservoir. Three uv absorbing peaks were eluted off of the column. The fractions of the third peak were pooled and reduced to dryness in vacuo. The residue was co-distilled twice with MeOH to give 550 mg of solid. An analytical sample of the Na salt was prepared by passing 150 mg of the free acid through a 50 ml column of Dowex 50 ($Na^+$). The column eluate was reduced to dryness in vacuo and the residue crystallized from EtOH and dried to yield 112 mg of 11; $\lambda_{max}^{pH\ 1}$ 281 nm, 291 sh ($\epsilon$ 21,800, 15,500), $\lambda_{max}^{pH\ 7}$ 277 nm, 280 ($\epsilon$ 22,400, 19,200), $\lambda_{max}^{pH\ 11}$ 277 nm, 280 ($\epsilon$ 22,400, 19,200), $\lambda_{max}^{pH\ 13}$ 299 nm ($\epsilon$ 21,600). Anal. ($C_{14}H_{16}N_7O_8BrNap.H_2O$) C, H, N, Na.

EXAMPLE 9

8-Benzylthio-$N^6$,2′-O-bis-(N-phenulcarbamoyl) adenosine 3′,5′-cyclic phosphate sodium salt (12).

A solution of 2 g (4.5 mmole) of 8-benzylthioadenosine 3′,5′-cyclic phosphate sodium salt (14)[12] and 3ml phenylissocyanate in 50 ml of DMF was heated at 70° overnight. The solution was partitioned between 150 ml of $H_2O$ and 150 ml of EtOAc. The aqueous phase was heated on a steam bath and extracted twice with EtOAc while hot. The solid which separated out of the cold aqueous phase was filtered and washed with a small amount of cold $H_2O$. The solid was recrystallized from EtOH and dried to yield 1.4 g (43%) of 12; $\lambda_{max}^{pH\ 1}$ 309 ($\epsilon$ 17,500), $\lambda_{max}^{pH\ 7}$ 295 nm ($\epsilon$ 20,000), $\lambda_{max}^{pH\ 11}$ 298 nm ($\epsilon$ 24,800), $\lambda_{max}^{pH\ 12.8}$ 321 nm ($\epsilon$ 31,000 ). Solutions of 12 were opaque and $\epsilon$ values are therefore minimum values). Anal. ($C_{31}H_{27}N_7O_8NaPS.\frac{1}{2}H_2O$) C, H, N, Na, S.

EXAMPLE 10

8-Benzylthio-$N^6$-(N-phenylcarbamoyl)adenosine 3′,5′-cyclic phosphate (15).

A solution of 0.6 g (.83 mmole) 8-benzylthio-$N^6$,2′-O-bis-(N-phenylcarbamoyl)adenosine 3′,5′-cyclic phosphate sodium salt (12) in 6 ml of DMF and 4 ml 2 N NaOH was stirred at room temperature for 2.5 hr. The solvent was removed in vacuo and the residue was partitioned between 50 ml of hot $H_2O$ and 50 ml of EtOAc. The hot aqueous phase was extracted two times with 50 ml of EtOAc. EtOH (50 ml) was added to the aqueous solution and the pH was adjusted to 2 with 1 N HCl. The gelatinous solid which formed was filtered, washed with 10 ml $H_2O$ and dissolved in 20 ml of EtOH. The solution volume was reduced to 10 ml, cooled and the solid filtered and dried to yield 220 mg (45%) of 15; $\lambda_{max}^{pH\ 1}$ 308 nm ($\epsilon$ 27,900), $\lambda_{max}^{pH\ 7}$ 296 nm ($\epsilon$ 31,200), $\lambda_{max}^{pH\ 11}$ 296 nm ($\epsilon$ 31,200), $\lambda_{max}^{pH\ 11}$ 296 nm ($\epsilon$ 30,300), $\lambda_{max}^{pH\ 12.75}$ 320 nm ($\epsilon$ 32,800). Anal. ($C_{24}H_{23}N_6O_7PS.H_2O$) C, H, N, S.

EXAMPLE 11

N⁶,2'-O-bis-(N-Methylcarbamoyl)-8-mercaptoadenosine 3',5'-cyclic phosphate sodium salt (16).

A solution of 700 mg of N⁶,2'-O-bis-(N-methylcarbamoyl)-8-bromoadenosine 3',5'-cyclic phosphate (11) and 700 mg of thiourea in 50 ml of H$_2$O containing 5 drops of formic acid was refluxed for 1 hr. After cooling, the pH was adjusted to 8.5 with 1 N NaOH. The solvent was distilled off in vacuo and 3 g of silica gel added to the residue. The residue was suspended in MeOH and the MeOH evaporated in vacuo. The final residue was added to a 15 g column (2.5 cm D.) of silica gel (packed in CHCl$_3$). The column was washed with CHCl$_3$ to remove thiourea and then the product was eluted off with MeOH:CHCl$_3$ (1:3). The solvent was removed in vacuo and the residue suspended in EtOH, filtered and dried, yielding 300 mg (45%) of 16; $\lambda_{max}^{pH\ 1}$ 244 nm, 313 ($\epsilon$ 19,800, 33,800), $\lambda_{max}^{pH\ 7}$ 233 nm, 312 ($\epsilon$ 17,800, 30,800), $\lambda_{max}^{pH\ 11}$ 233 nm, 311 ($\epsilon$ 17,500, 29,600). Anal. (C$_{14}$H$_{17}$N$_7$O$_8$NaPS.1¾ H$_2$O) C, H, N, S.

Preferred carbamoyl compounds prepared as in the preceding examples were assayed for ability to activate protein kinase by the procedure described in K. Muneyama et al, Biochem. 10, 2390 (1971), using bovine brain C-AMP dependent kinase purified according to Kuo & Greengard, in Proc. Nat. Acad. Sci. U.S.A. 64, 1349 (1969). Compounds 6, 7 and 15 proved superior in kinase activation to C-AMP itself and, indeed, compound 7 activated bovine brain protein kinase approximately five times better than C-AMP (Ka'=4.9, where Ka is the activation constant determined from a Lineweaver-Burk plot and Ka' = K$_a$ for C-AMP/K$_a$ for test compound). The highest value for Ka' previously reported in the literature was 3.77, for the 8-thio derivative of C-AMP. K. Muneyama et al, supra.

When tested for vulnerability to degradation by rabbit kidney high K$_m$ C-AMP phosphodiesterase according to the procedure of J. P. Miller et al, Biochem. 12, 1010 (1973), all of compounds 2, 3, 4, 5, 6, 7, 8, 11, 12, 15 and 16 proved more resistant to hydrolysis than C-AMP. In fact, hydrolysis to any appreciable extent could be detected only in the case of compound 8 (hydrolysis at a rate only 8% that of C-AMP).

Certain of the preferred compounds proved equal to or superior to theophylline as inhibitors of one or both of beef heart and rabbit lung phosphodiesterase in assay by the method of J. P. Miller et al, supra. The results appear in Table I below.

TABLE I

Inhibition of Beef Heart and Rabbit Lung cAMP Phosphodiesterases

| Compound | I$_{50}$ ($\mu$M) | |
|---|---|---|
| | Beef Heart | Rabbit Lung |
| 11 | 260 | 130 |
| 7 | 22 | 160 |
| 4 | 93 | 190 |
| 12 | 22 | 10 |
| 15 | 14 | 21 |
| 8 | 130 | 210 |
| Theophylline | 130 | 230 |

In addition to the foregoing, compounds 5, 6, 7 and 8 have been shown to activate steroidogenisis and lipolysis at concentrations substantially lower than C-AMP. Compounds 7, 15, and their 2'-O-butyryl derivatives inhibit adenyl cyclase, suggesting employment in treatment of cholera and as immunosuppressive or anti-inflammatory agents (see Shuman et al application Ser. No. 368,323, filed June 8, 1973, now U.S. Pat. No. 3,853,303, the disclosure of which is incorporated herein by reference). Compounds 5, 6, 8 and 15 act to lower blood pressure, and compound 7 as an inotropic agent has proven persistent in action and the equal of aminophylline in increasing cardiac output, without deleteriously affecting heart rate.

We claim:

1. A compound of structure

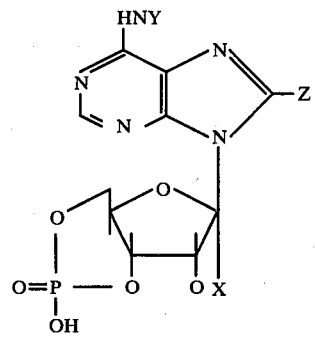

wherein Y is COOR$_1$, CONHR$_1$, or CONHC$_6$H$_5$, X is C$_1$-C$_{18}$ acyl, Y or H, Z is H, bromine, chlorine or SR$_2$, R$_1$ is C$_1$-C$_6$ alkyl and R$_2$ is H, phenyl, benzyl or C$_1$-C$_6$ alkyl.

2. A compound according to claim 1 wherein X is acyl or H.

3. A compound according to claim 2 wherein Y is CONHR$_1$ or CONHC$_6$H$_5$.

4. A compound according to claim 3 wherein Y is CONHC$_6$H$_5$.

5. N⁶-(N-methylcarbamoyl) adenosine 3',5'-cyclic phosphate.

6. N⁶-(N-propylcarbamoyl) adenosine 3',5'-cyclic phosphate.

7. N⁶-(N-phenylcarbamoyl) adenosine 3',5'-cyclic phosphate.

8. N⁶-(ethoxycarbonyl) adenosine 3',5'-cyclic phosphate.

9. 8-Benzylthio-N⁶-(N-phenylcarbamoyl) adenosine 3',5'-cyclic phosphate.

10. 8-Benzylthio-2'-O-butyryl-N⁶-(N-phenylcarbamoyl) adenosine 3',5'-cyclic phosphate.

11. 2'-O-butyryl-N⁶-(N-phenylcarbamoyl) adenosine 3',5'-cyclic phosphate.

12. A compound of the formula

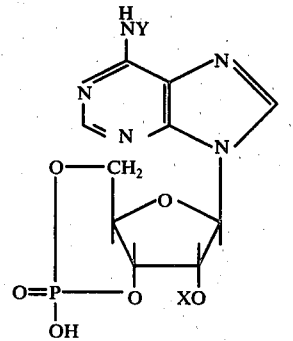

wherein Y is selected from the group consisting of COOR$_1$, CONHR$_1$ and CONHC$_6$H$_5$; X is selected from the group consisting of COOR$_1$, CONHR$_1$, CONHC$_6$H$_5$, C$_1$-C$_4$ acyl and H and R$_1$ is lower alkyl.

13. A compound according to claim 12 wherein X is acyl or H.

14. A compound according to claim 12 wherein X is H.

15. A compound according to claim 13 wherein Y is $CONHR_1$.

16. A compound according to claim 13 wherein Y is $CONHC_6H_5$.

17. A compound according to claim 15 wherein $R_1$ is $C_1$–$C_3$ alkyl.

18. A compound according to claim 16 wherein $R_1$ is $C_1$–$C_3$ alkyl.

19. A compound according to claim 14 wherein Y is $CONHR_1$.

20. A compound according to claim 14 wherein Y is $CONHC_6H_5$.

21. A compound according to claim 15 wherein $R_1$ is $C_1$–$C_3$ alkyl.

22. A compound according to claim 16 wherein $R_1$ is $C_1$–$C_3$ alkyl.

* * * * *